United States Patent
Brilliant

[19]

[11] Patent Number: 5,957,687
[45] Date of Patent: Sep. 28, 1999

[54] APPARATUS AND METHOD FOR DETECTING DENTAL PLAQUE

[75] Inventor: Herbert Brilliant, Philadelphia, Pa.

[73] Assignee: Plak-Lite Company LLC, Wayne, Pa.

[21] Appl. No.: 09/119,552

[22] Filed: Jul. 21, 1998

[51] Int. Cl.$^6$ .................................................. A61C 1/00
[52] U.S. Cl. ........................................... 433/31; 600/248
[58] Field of Search ................................. 433/29, 31 R; 600/248

[56] References Cited

U.S. PATENT DOCUMENTS

| | | | |
|---|---|---|---|
| 922,078 | 5/1909 | Benson | 600/248 |
| 2,066,313 | 1/1937 | Barr | 433/31 |
| 3,309,274 | 3/1967 | Brilliant | 424/49 |
| 3,459,178 | 8/1969 | Fleming | 600/248 |
| 3,711,700 | 1/1973 | Westlund, Jr. et al. | 240/41.15 |
| 4,592,726 | 6/1986 | Brilliant | 433/31 |
| 4,872,838 | 10/1989 | Canter et al. | 433/31 |

Primary Examiner—John J. Wilson
Attorney, Agent, or Firm—William H. Eilberg

[57] ABSTRACT

A hand-held diagnostic unit simplifies the process of monitoring the teeth for the presence of plaque, or other foreign matter, in the oral cavity. The unit includes a source of filtered light and a mirror, both contained within the same housing. The mirror is inclined relative to the front vertical wall of the housing, and a spring-loaded switch on the housing activates the light. The user coats the teeth with a substance which fluoresces when illuminated with light of the proper frequency, and which therefore enhances the visibility of plaque. The user holds the diagnostic unit opposite the teeth, activates the light, and points the unit so as to direct light towards the area of interest, while monitoring the teeth by looking at the mirror of the diagnostic unit. The inclination of the mirror makes it easy to view most areas of the mouth and to determine whether plaque is present. The diagnostic unit can therefore be operated with one hand, and can be easily transported from one location to another. The invention therefore provides an easy procedure by which an unassisted user can monitor the effectiveness of plaque-control measures.

6 Claims, 5 Drawing Sheets

APPARATUS AND METHOD FOR DETECTING DENTAL PLAQUE

BACKGROUND OF THE INVENTION

This invention relates to the field of dental hygiene, and provides a device and method for monitoring the presence of plaque, or other foreign matter, on the teeth.

The dental profession has educated the general public on the importance of removal of dental plaque. Bacterial plaques are known to cause periodontal disease, and various methods of plaque removal have been recommended, such as flossing, rinsing with specially formulated mouthwashes, etc.

Regardless of which plaque-removal technique is used, the problem is that the patient has no reliable way of evaluating the effectiveness of his or her plaque-removal efforts. The patient may believe that he or she has diligently flossed, but there still could be a considerable amount of plaque remaining on the teeth, and the patient has no way of knowing how much there is, without visiting a dentist.

There have been various methods proposed, in the prior art, for indicating the condition of the teeth. It is known, for example, that certain substances become fluorescent when illuminated by light having a particular frequency. Such substances, when applied to body tissues such as teeth, can greatly enhance the visibility of foreign matter on those tissues, when the tissues are exposed to light of the proper frequency. Thus, it has been proposed to coat the teeth with a fluorescent dye, or similar solution, and to illuminate the teeth to reveal the quantity of plaque that may have accumulated. Methods based on this principle are described in U.S. Pat. Nos. 3,309,274, 3,711,700, and 4,592,726, the disclosures of which are incorporated by reference herein.

While the above-described procedures do reveal the condition of the teeth, the methods of the prior art are rather awkward for use by an unassisted person. For this reason, the average person is unlikely to use such methods regularly. To examine the teeth for plaque, the user must shine a light in exactly the right place, and must hold a separate mirror (such as that described in U.S. Pat. No. 4,592,726) at exactly the proper angle, in order to obtain meaningful results. Proper positioning of the light source and mirror is essentially a matter of trial and error, and is therefore very inconvenient for the average user. The problems inherent with a hand-held mirror could be avoided by using a wall-mounted mirror, but it is generally very difficult to inspect the areas of interest using a stationary, vertically-oriented mirror.

The present invention solves the above-described problems by providing a method and apparatus for reliably determining the presence of plaque, or other foreign matter, on the teeth. The present invention makes it very easy for an unassisted person to determine the condition of the teeth, and makes it more likely that such a procedure will be used frequently.

SUMMARY OF THE INVENTION

The present invention therefore includes a method of detecting dental plaque, or other foreign matter, which is normally invisible to the naked eye. According to this method, the user first coats the teeth with a substance which, when illuminated with light of the proper frequency, causes plaque to become more readily visible. Then, the user holds a diagnostic unit to face the teeth. The diagnostic unit includes a housing which contains a source of light and a mirror, the mirror being inclined relative to the vertical wall of the diagnostic unit. Then, by pressing a spring-loaded switch on the diagnostic unit, the user activates the source of light. The light illuminates the teeth, and the user observes the condition of the teeth by looking at the mirror in the diagnostic unit. The angle of inclination of the mirror makes it easy for the user to observe most or all of the illuminated teeth. The method can be easily practiced with one hand, because the diagnostic unit contains both a mirror and a light source.

For regions of the mouth which still cannot be easily observed with the mirror of the diagnostic unit, one can use a small auxiliary mirror, which can be manipulated as necessary.

The invention also includes the diagnostic unit itself. The mirror is preferably inclined at an angle in the range of about 5°–15°, and preferably about 10°. The angle of inclination is measured relative to the front vertical wall of the housing of the diagnostic unit. If the angle is within the above-described range, the user can normally view all of the illuminated teeth with ease.

In the preferred embodiment, the light is filtered light, so that it is concentrated in a desired frequency range, such as blue. The solution applied to the teeth is preferably a material which fluoresces when exposed to such filtered light. The filtered light is preferably produced by a filter material which defines a cover for the light source of the diagnostic unit.

The diagnostic unit includes a housing which, in the preferred embodiment, is shaped to make it easy to grip. It is important that the unit be operable by an unassisted person, and therefore it is necessary to provide a unit which can be held and operated with one hand.

The present invention therefore has the primary object of providing an apparatus and method for detecting plaque, or other foreign matter, on a user's teeth.

The invention has the further object of providing a method for detecting dental plaque, which method can be practiced by an unassisted user.

The invention has the further object of promoting dental health by making it easy for persons to monitor the effectiveness of their plaque-removal efforts.

The invention has the further object of providing a hand-held diagnostic unit for simplifying the monitoring of plaque on the teeth.

The invention has the further object of providing a lightweight and compact device for monitoring the condition of the teeth, wherein the device can be readily transported from one location to another.

The invention has the further object of providing an apparatus which simplifies and makes practical the use of solutions which indicate the presence of plaque when exposed to light.

The reader skilled in the art will recognize other objects and advantages of the present invention, from a reading of the brief description of the drawings, the detailed description of the invention, and the appended claims.

DETAILED DESCRIPTION OF THE INVENTION

The present invention includes a diagnostic unit, and a method of using the diagnostic unit, for determining the amount of plaque, or other foreign matter, on the teeth.

Figure 1:
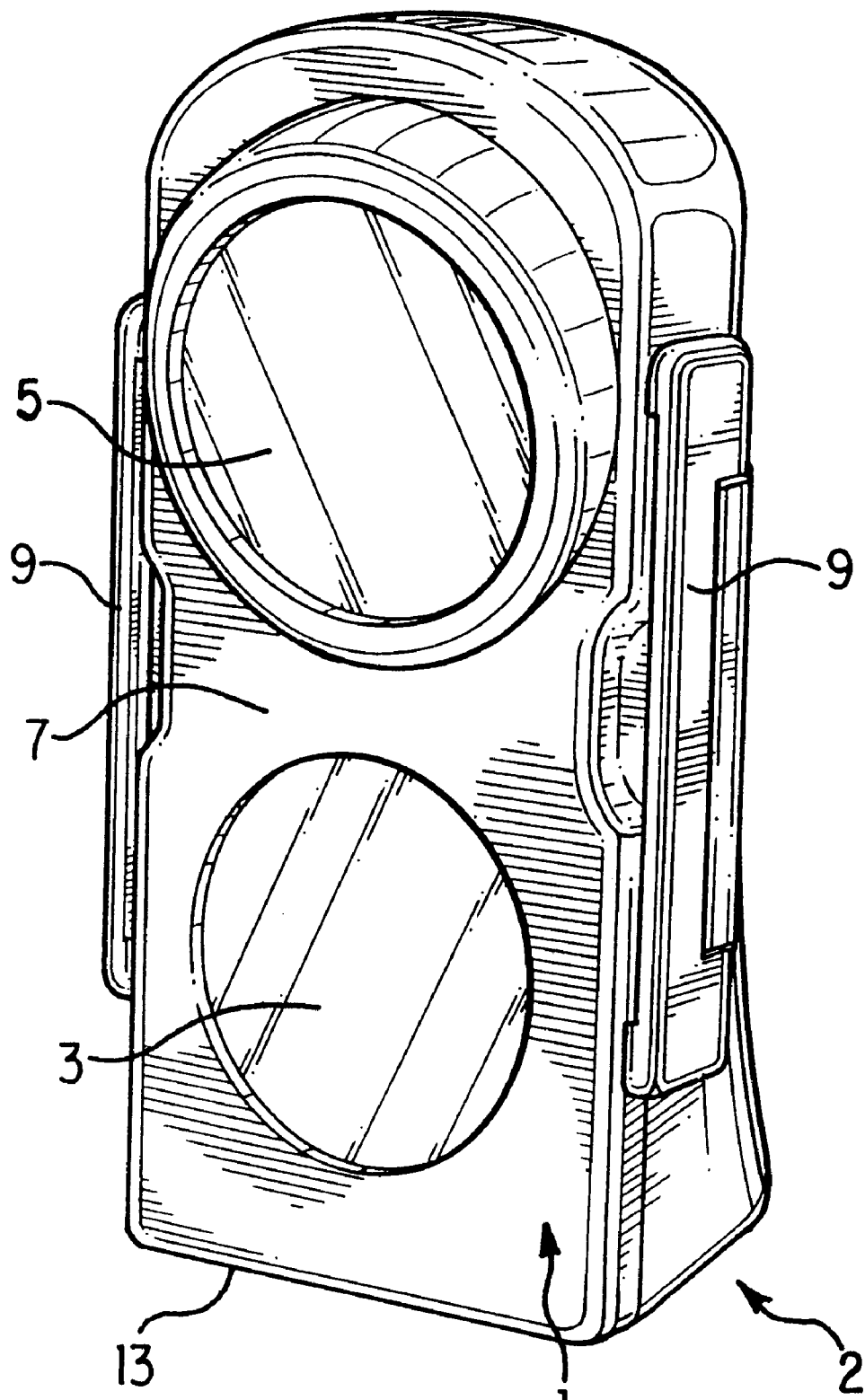
FIG. 1 provides a perspective view of the diagnostic unit of the present invention.

FIG. 1 provides a perspective view of the diagnostic unit. The diagnostic unit 2 includes housing 1 which supports optical filter 3 and mirror 5. The optical filter can be a piece of tinted glass or tinted translucent plastic. The filter also serves as a cover for a light source (not shown), which can be an incandescent bulb located behind the filter. The bulb could be the same type of bulb which is found in an ordinary flashlight. The filter converts white light from the light source into light of a desired frequency, or of a desired frequency range. The filter and mirror are mounted on front vertical wall 7 of housing 1. The filter is substantially parallel to the wall 7, and the mirror is inclined at an angle to the wall, the upper portion of the mirror being tilted forward relative to the user, as shown. Brackets 9 enable the diagnostic unit to be mounted or held in a desired location. The housing also includes a flat bottom 13 (more clearly visible in FIG. 2) which allows the housing to stand on a flat surface.

Figure 2:
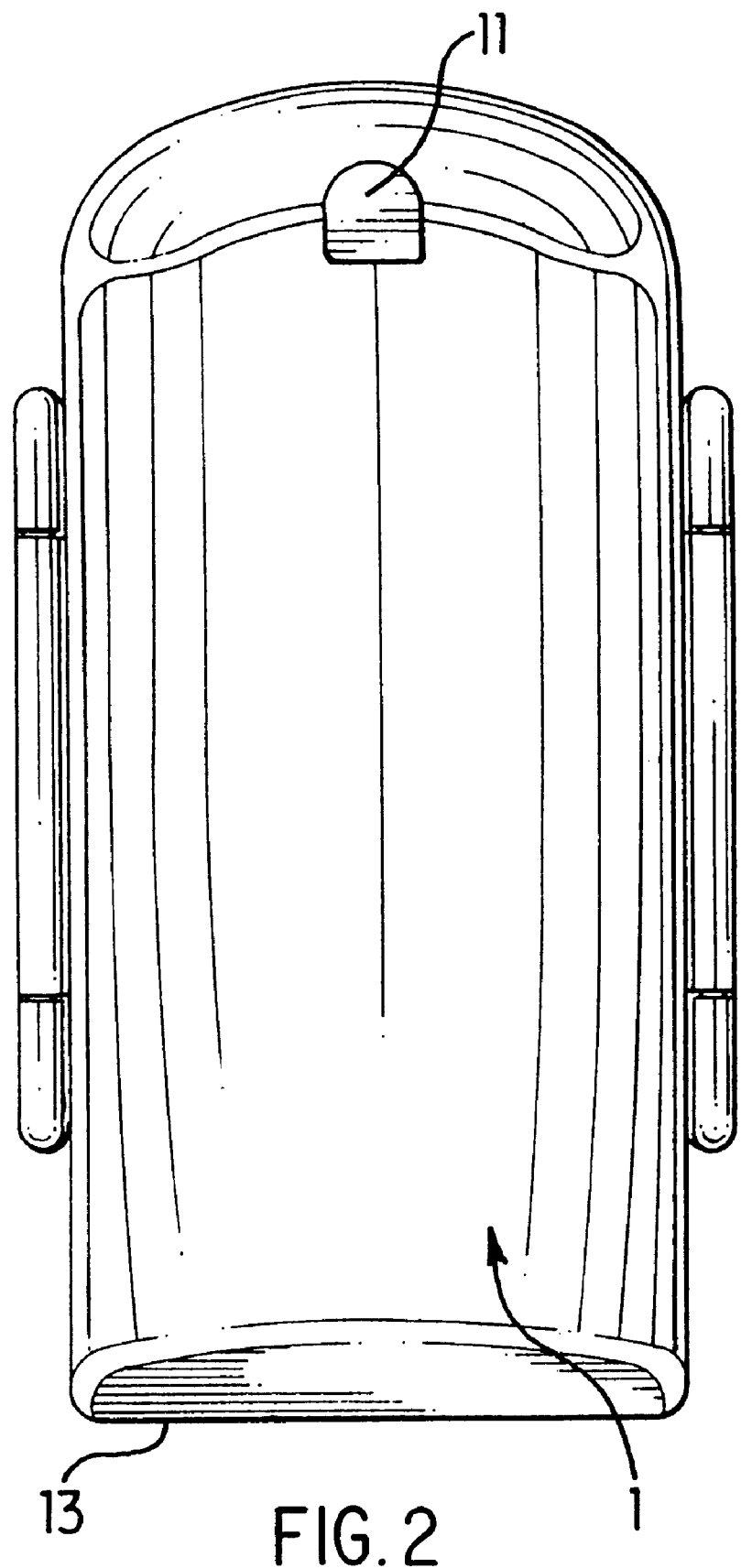
FIG. 2 provides a rear elevational view of the diagnostic unit of the present invention, showing the switch which activates the light source.

The rear elevational view of FIG. 2 shows switch 11, mounted in the rear portion of housing 1. The switch is connected to activate the light source located inside the housing. A battery or equivalent power source (not shown) is also located inside the housing, to provide power for the light source. The bulb is connected in series with the switch and the battery, in a conventional manner. The switch is preferably spring-loaded, and normally open, so that upon depressing it with slight pressure of the finger, the light is activated, and when finger pressure is released, the light turns off.

The drawings, especially FIGS. 1, 2, 4, and 5, show various features of the preferred embodiment of the apparatus of the present invention. In particular, the rear side of the lower portion of the housing flares outwardly, such that the thickness of the housing becomes progressively greater towards the lower portion of the housing. The flare of the housing is substantially continuous from the upper portion to the lower portion of the housing. The drawings also show that the thickness of the housing at the lower portion is less than twice the thickness of the housing at the upper portion. Also, the rear side of the housing has a smoothly convex surface.

Figure 3:
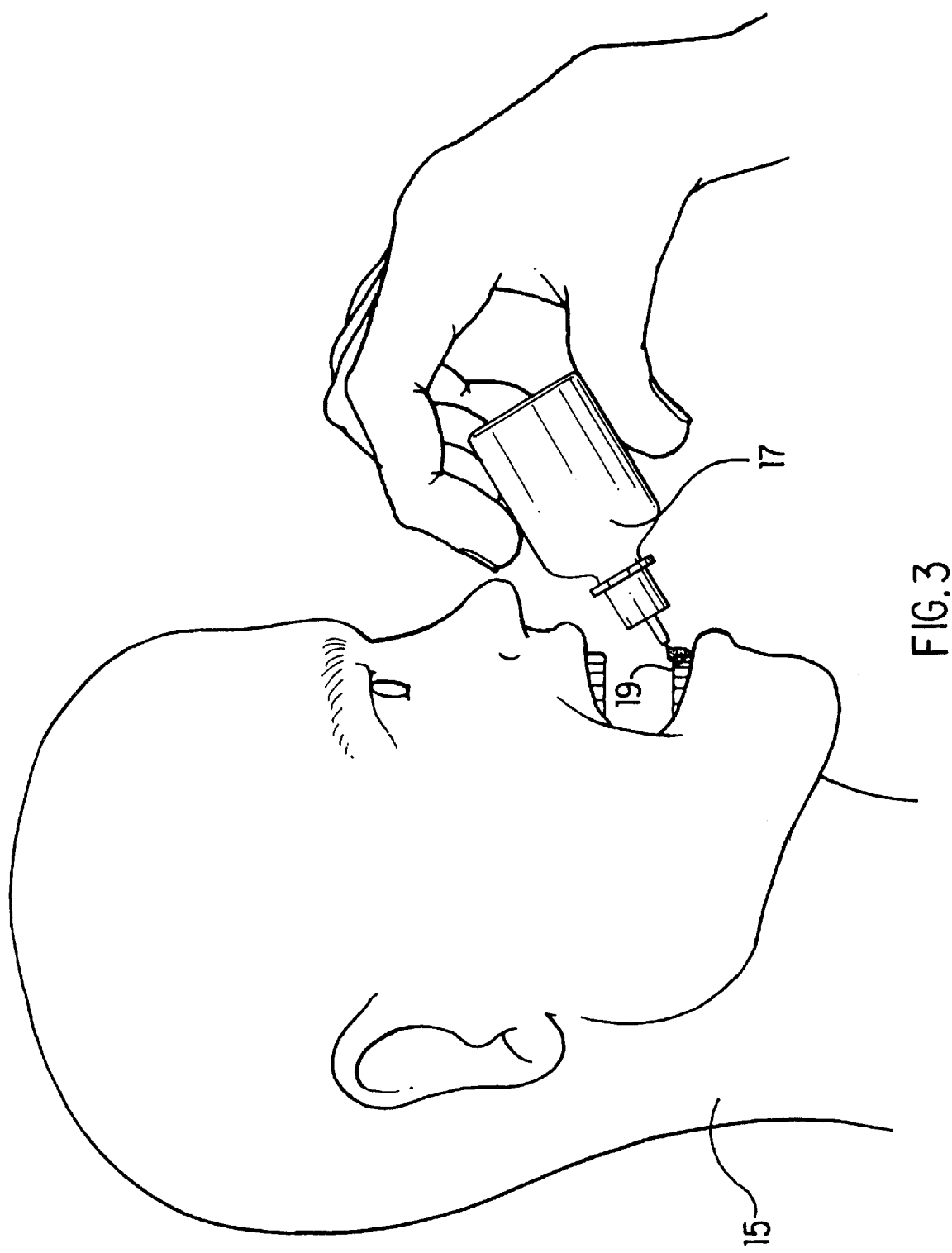
FIG. 3 provides a side elevational view showing a user coating his teeth with a solution which renders plaque more clearly visible when exposed to filtered light, in a preliminary step of the method of the present invention.
Figure 4:
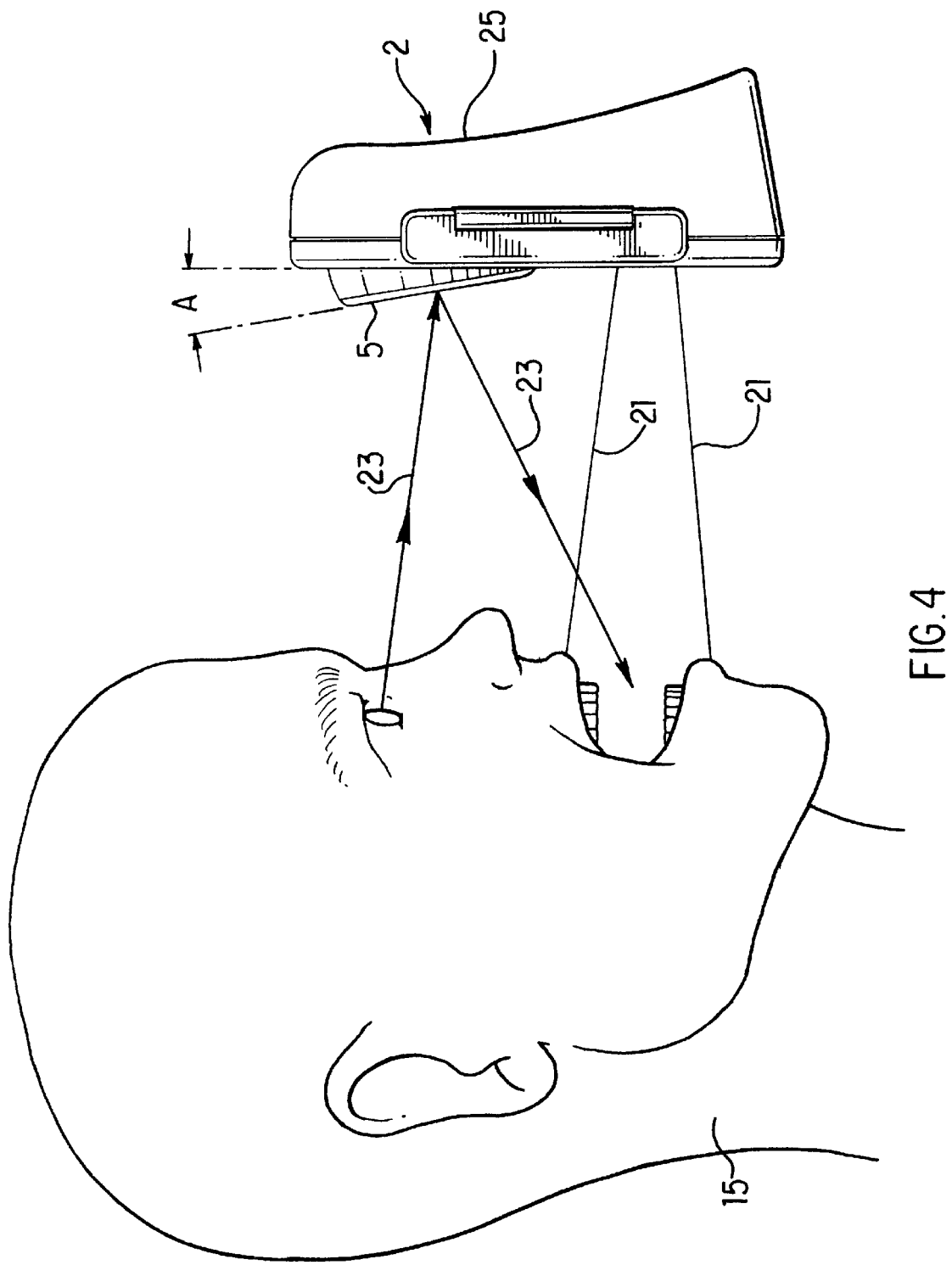
FIG. 4 provides a side elevational view showing the geometrical relationships between the user and the hand-held diagnostic unit of the present invention.
Figure 5:
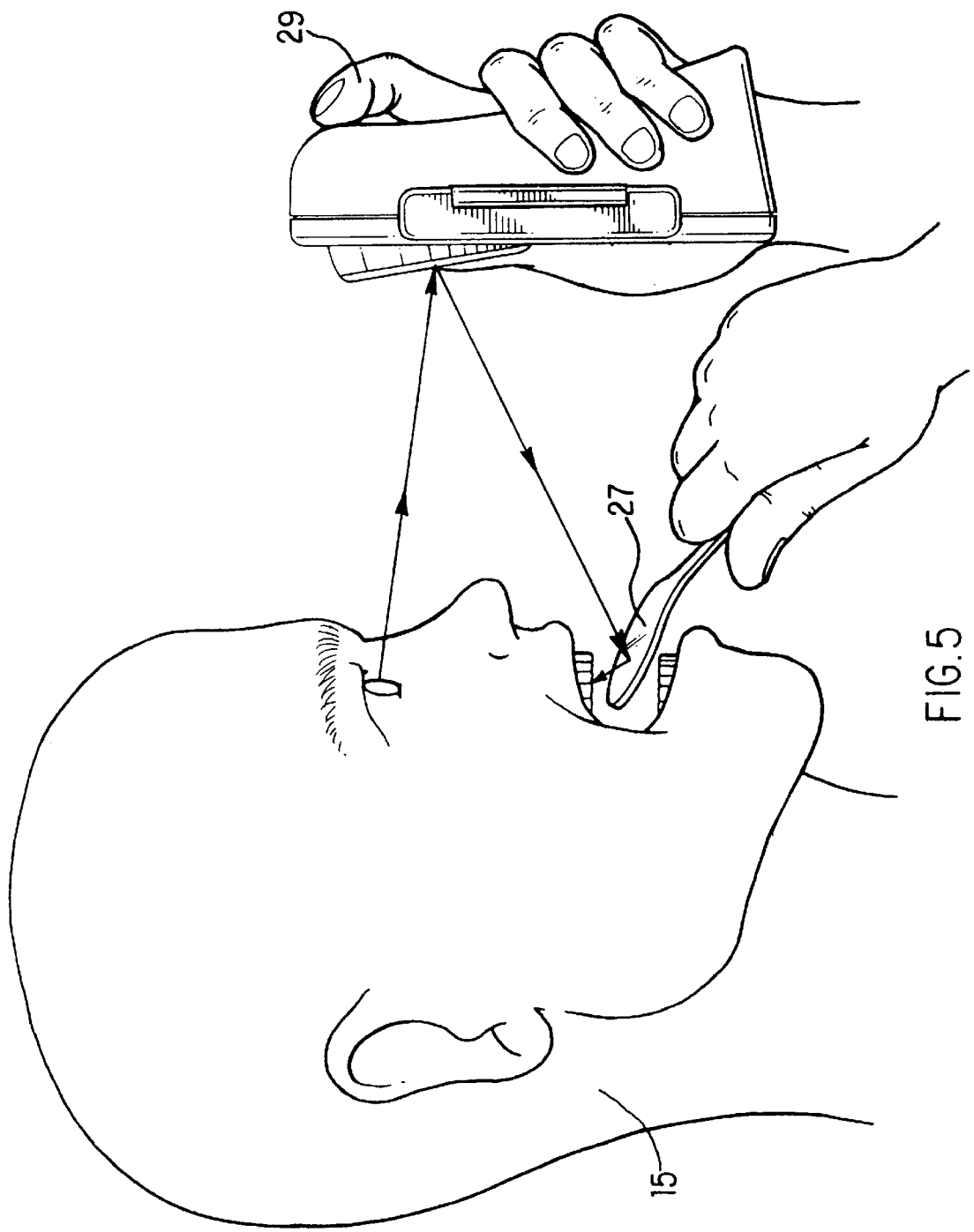
FIG. 5 provides a side elevational view showing the user actuating a light source in the hand-held diagnostic unit, and also manipulating an auxiliary mirror, according to the present invention.

FIGS. 3–5 show the steps included in the method of the present invention. FIG. 3 depicts the preliminary step of coating the teeth with a solution which makes plaque on the teeth more readily visible when the solution is illuminated by an appropriate light source. In FIG. 3, user 15 applies the solution contained in bottle 17 to the teeth 19, coating those portions which the user desires to evaluate. After applying the solution, it is desirable for the user to agitate the solution throughout the oral cavity to insure more complete and uniform distribution on the teeth. The solution has a composition which makes it adhere to plaque on the teeth. The solution could be one of solutions described in the above-cited patents.

The solution is preferably chosen to be a substance which fluoresces when illuminated by light of a particular frequency, or of a particular frequency range, as described in any one of the patents cited above. However, the invention is not limited to any particular formulation; the specific composition of the solution does not form part of the present invention. Any material which enhances the visibility of plaque, or other foreign matter, when exposed to light, could be used in the present invention.

The filter in the diagnostic unit is chosen to provide light at the desired frequency, to make the solution fluoresce and to indicate the presence of plaque.

FIG. 4 illustrates the geometrical relationships which make the present invention work. As shown in FIG. 4, the diagnostic unit 2 is held facing the user. For clarity of illustration, the user's hand is not shown gripping the diagnostic unit, but the manner of gripping can be as shown explicitly in FIG. 5. Lines 21 indicate the paths taken by light from the light source (located inside the diagnostic unit). The light illuminates the oral cavity of the user. Lines 23 indicate the path taken by light traveling between the user's eye and mouth, with the assistance of mirror 5. As indicated in FIG. 4, the inclination of the mirror, relative to the front vertical wall of the diagnostic unit, makes it easy for the user to observe the oral cavity while shining light into that cavity.

The inclination of the mirror is defined as the angle between the surface of the mirror and the front vertical wall of the diagnostic unit. This angle is designated as angle A in FIG. 4. The optimum value of angle A is in the range of about 5°–15°, the most preferred value being about 10°. However, the invention is not limited to a particular angle. Variations in the angle may be appropriate for users having different head sizes.

The housing of the diagnostic unit is preferably shaped to facilitate gripping by the user's hand. In particular, the housing includes a tapered rear surface 25. FIG. 5 shows the user gripping the diagnostic unit. It is advantageous to provide a unit which can be operated with one hand, so as to enable the user to brush away illuminated plaque with the other hand.

FIG. 5 also shows auxiliary mirror 27, which is separate from the mirror contained in the diagnostic unit. There may be some areas in the oral cavity which are not readily visible through the mirror of the diagnostic unit. The auxiliary mirror is provided for these areas, and this mirror may be manipulated by the user as shown.

FIG. 5 also shows the user's finger 29 actuating the spring-loaded switch to activate the light source.

Note that in the ordinary practice of the invention, wherein the auxiliary mirror is not needed, the self-diagnosis can be performed with one hand. The diagnostic unit can be made sufficiently light in weight that holding it with one hand requires no substantial effort. Since the mirror and the light source are contained within the same housing, the user can hold that housing with one hand, while activating the light source (as illustrated in FIG. 5), illuminating the oral cavity, and viewing the oral cavity with the mirror of the diagnostic unit. In the event that an area cannot be seen with the latter mirror, the user can manipulate the auxiliary mirror. Thus, in the normal case, only one hand is needed. In a more difficult case, both hands can be used.

The present invention therefore greatly simplifies the process of evaluating the condition of the teeth. It avoids the need to guess at the proper position of the light source and mirror, since both of these components are provided in a single hand-held unit, and are mounted and oriented, relative to each other, in the optimum way. The diagnostic unit is compact and lightweight, and can therefore be easily transported. Thus, a user can practice the method at home and at work, and can carry the unit from one location to another. By activating a switch, the user obtains immediate information on the amount and distribution of plaque in the mouth.

The invention can be modified in various ways. The composition of the solution can be varied. The exact shape of the filter and/or mirror could be modified. For example, the mirror and filter could be square instead of circular. The specific design and location of the switch which activates the light source could also be changed. Though the invention has been described primarily with respect to the detection of plaque, it is not limited to plaque, but it can be used to detect other tooth-accumulated material, or other foreign matter in the oral cavity. These and other modifications, which will be apparent to the reader skilled in the art, should be considered within the spirit and scope of the following claims.

What is claimed is:

1. Apparatus for detecting foreign matter in the oral cavity, comprising:
   a) a housing, the housing having an upper portion and a lower portion, the housing also having a front side and a rear side, the housing having a thickness defined by a distance between the front side and the rear side,
   b) a mirror disposed in the upper portion, and on the front side, of the housing,
   c) an optical filter disposed in the lower portion, and on the front side, of the housing,
   d) a light source located within the housing and behind the optical filter, and
   e) means for activating the light source,
   wherein the rear side of the lower portion of the housing flares outwardly, such that the thickness of the housing becomes progressively greater towards the lower portion of the housing.

2. The apparatus of claim 1, wherein the rear side of the housing has a flare which is substantially continuous from the upper portion to the lower portion of the housing.

3. The apparatus of claim 1, wherein the thickness of the housing at the lower portion is less than twice the thickness of the housing at the upper portion.

4. The apparatus of claim 1, wherein the rear side of the housing defines a smoothly convex surface.

5. Apparatus for detecting foreign matter in the oral cavity, comprising:
   a) a housing, the housing having an upper portion and a lower portion, the housing also having a front side and a rear side, the housing having a thickness defined by a distance between the front side and the rear side,
   b) a mirror disposed in the upper portion, and on the front side, of the housing,
   c) an optical filter disposed in the lower portion, and on the front side, of the housing,
   d) a light source located within the housing and behind the optical filter, and
   e) means for activating the light source,
   wherein the rear side of the lower portion of the housing flares outwardly, such that the thickness of the housing becomes progressively greater towards the lower portion of the housing,
   wherein the rear side of the housing has a flare which is substantially continuous from the upper portion to the lower portion of the housing, and
   wherein the rear side of the housing defines a smoothly convex surface.

6. The apparatus of claim 5, wherein the thickness of the housing at the lower portion is less than twice the thickness of the housing at the upper portion.

* * * * *